United States Patent [19]

Liautaud et al.

[11] 4,387,092

[45] Jun. 7, 1983

[54] PROCESS FOR THE PREPARATION OF FACTOR VIII CONCENTRATE

[75] Inventors: Jacques Liautaud, Limonest, France; Edward Shanbrom, Santa Ana, Calif.

[73] Assignee: Societe Anonyme dite: L'Oreal, Paris, France

[21] Appl. No.: 237,135

[22] PCT Filed: Jun. 30, 1980

[86] PCT No.: PCT/FR80/00102

§ 371 Date: Feb. 11, 1981

§ 102(e) Date: Feb. 11, 1981

[30] Foreign Application Priority Data

Jun. 29, 1979 [FR] France ................................ 79 16966

[51] Int. Cl.$^3$ ............................................... A61K 35/14
[52] U.S. Cl. .................................. 424/101; 260/112 R
[58] Field of Search ..................... 424/101; 260/112 R

[56] References Cited

U.S. PATENT DOCUMENTS

| | | |
|---|---|---|
| 3,631,018 | 12/1971 | Shanbrom et al. .................. 424/177 |
| 3,770,631 | 11/1973 | Fekete et al. ....................... 424/101 |
| 4,069,216 | 1/1978 | Shanbrom ........................... 424/101 |
| 4,085,095 | 4/1978 | Bick et al. ........................... 424/101 |

FOREIGN PATENT DOCUMENTS

| | | |
|---|---|---|
| 1350895 | 1/1964 | France . |
| 1589414 | 5/1970 | France . |
| 2348702 | 11/1977 | France . |
| 2363577 | 3/1978 | France . |

*Primary Examiner*—Sam Rosen
*Attorney, Agent, or Firm*—Cushman, Darby & Cushman

[57] ABSTRACT

An improved process for preparing factor VIII concentrate which comprises a first stage wherein fibrinogen is precipitated from a buffered plasma or plasma cryoprecipitate solution by the addition of a polyol and a second stage where factor VIII is precipitated from the resulting supernatant also by the addition of a polyol. The improvement in the first stage resides in adding the polyol in an amount of 1–3% and maintaining the temperature of the buffered solution between about 2°–4° C.

7 Claims, No Drawings

PROCESS FOR THE PREPARATION OF FACTOR VIII CONCENTRATE

In U.S. Pat. No. 4,069,216 there is described and claimed a process for preparing a factor VIII concentrate wherein it comprises the stage consisting in maintaining a buffer solution containing factor VIII and about 6% polyol at a temperature of about 0° to 5° C. until precipitation occurs.

The resulting precipitate is made up of concentrated, purified factor VIII or antihemophilic factor, also called AHF.

According to a particular embodiment, also described and claimed in the aforementioned patent, this process is preceded by a stage consisting in using a plasma solution or plasma cryoprecipitate as the starting product and adding about 4% polyol to said solution, eliminating the resulting fibrinogen precipitate and using the supernatant as the starting product in the process mentioned above.

This preliminary stage was performed at a temperature of about 20° to 30° C.

It has now been discovered that this preliminary purification stage can be replaced by another preliminary stage that consists in treating a factor VIII solution to be purified with a slight amount of polyol corresponding to a concentration less than 4%, while cooling at a temperature below 15° C. Thus, the major part of the fibrinogen and other impurities such as, for example, cold insoluble globulins (CIG) are eliminated by precipitation. By operation at low temperature, a purification is obtained at least as good as with the process at ambient temperature of the aforementioned patent, while a smaller amount of polyol is used.

According to preferred embodiments, this preliminary stage of the present invention can further be characterized by the following points, taken individually or in combination.

The starting product, such as those mentioned in the aforementioned patent, is used in the form of a buffer solution containing factor VIII to be purified; the starting product is, for example, a cryoprecipitate buffer solution or a plasma solution containing factor VIII. The impurities present in the starting product are fibrinogen and CIGs.

Said starting solution is buffered at a pH between 6 and 7, and preferably 6.0 to 6.5.

Polyol is added, preferably in a concentration of about 1 to 3%.

In a general way, the indications of concentrations, in the present invention, are by weight/volume.

The polyol can be, for example, polyethyleneglycol, preferably polyethyleneglycol 4000.

As other usable polyols, there will be cited in particular sequenced polymers of the polyoxyethylene-polyoxypropylene-polyoxyethylene type such as those sold under the name of Pluronic F-68.

Cooling is at a temperature between 0.5° and 15° C., generally between about +1° and +5° C. and in particular between about 2° and 4° C.

Stirring is for a time that can vary from 5 minutes to 3 hours, preferably for about an hour, while cooling is maintained to keep the selected temperature, then centrifuging is performed still while cooling at a temperature below 15° C., preferably between +1° and +5° C., as indicated above.

The resulting precipitate is eliminated and the supernatant is used as the starting product of the process described in said patent.

The following example illustrates the invention without, however, limiting it.

EXAMPLE

Cryoprecipitate (487 g) which is dissolved in 1920 ml of a buffer solution consisting of an aqueous solution of 0.02 M trisodium citrate and 0.1 M glycine with a pH 6.9 is used as the starting point.

After complete dissolving, the pH is adjusted to 6.4 with citric acid and PEG 4000 is added in a 2% concentration (38.4 g). Cooling is to +2° C. and stirring is performed for an hour. Centrifuging is done with the temperature kept at +2° C. The precipitate is eliminated and the supernatant collected (1670 ml).

Then the supernatant is treated according to the process of the aforementioned patent. For this, the pH of the supernatant is adjusted to 6.9 by addition of NaOH, then 68 g of PEG (6%) are added still at +2° C. After stirring to the end of precipitation, centrifuging is performed at +2° C. and the precipitate (14 g) of purified factor VIII is collected.

The precipitate is redissolved in 400 ml of a citrate-glycine buffer solution, the pH is adjusted to 6.9 and the solution is subjected to a sterilizing filtration through micropore membrane filters having, for example, pores of a diameter of 1.2-0.65-0.45 and 0.3 microns.

The resulting purified sterile factor VIII solution is lyophilized in the usual way.

We claim:

1. In a process for preparing Factor VIII concentrate where in a first stage fibrinogen is precipitated from a solution of plasma or plasma cryoprecipitate from a buffered solution having a pH ranging between 6 and 7 by the addition of a polyol and the precipitate comprising fibrinogen is removed to provide a supernatant comprising Factor VIII and in a second stage said Factor VIII is precipitated from said supernatant by increasing the polyol concentration to at least about 6% and holding the solution containing said increased amounts of polyol at from about 0° to about 5° until precipitation of said Factor VIII occurs, the improvement comprising the steps of in said first stage of precipitating fibrinogen from a solution of plasma or plasma cryoprecipitate from said buffered solution by the addition of a polyol in an amount of about 1 to 3% while cooling said solution to a temperature between about 2° and 4° C.

2. The process of claim 1 wherein said pH ranges from 6.0 to 6.5.

3. The process of claim 1 where in said first stage said buffered solution is stirred for a period of time ranging from 5 minutes to 3 hours while maintaining the temperature thereof at the selected temperature.

4. The process of claim 1 wherein the polyol is polyethylene glycol.

5. The process of claim 4 wherein said polyethyleneglycol is polyethyleneglycol 400.

6. The process of claim 1 wherein said polyol is a sequenced polymer of the polyoxyethylene-polyoxypropylene-polyoxyethylene type.

7. The process of claim 6 wherein said polyol is Pluronic-68.

* * * * *

UNITED STATES PATENT AND TRADEMARK OFFICE
CERTIFICATE OF CORRECTION

PATENT NO. : 4,387,092

DATED : June 7, 1983

INVENTOR(S) : Jacques Liautaud
Edward Shanbrom

It is certified that error appears in the above—identified patent and that said Letters Patent is hereby corrected as shown below:

On the title page

At Section [73] Assignee, please change the Assignee
   to read:

-- Societe Anonyme dite: Institut Merieux, Lyon, France--.

Signed and Sealed this

Twenty-seventh Day of March 1984

[SEAL]

Attest:

GERALD J. MOSSINGHOFF

Attesting Officer     Commissioner of Patents and Trademarks